United States Patent
Principe Nicolas et al.

(10) Patent No.: US 12,150,920 B2
(45) Date of Patent: *Nov. 26, 2024

(54) TOPICAL PHARMACEUTICAL COMPOSITION IN THE FORM OF AQUEOUS GEL COMPRISING AT LEAST AMITRIPTYLINE

(71) Applicant: AlgoTherapeutix, Suresnes (FR)

(72) Inventors: Paola Principe Nicolas, Cernay la Ville (FR); Frédéric Lallemand, Rambouillet (FR); Stéphane Thiroloix, Suresnes (FR)

(73) Assignee: ALGOTHERAPEUTIX, Suresnes (FR)

(*) Notice: Subject to any disclaimer, the term of this patent is extended or adjusted under 35 U.S.C. 154(b) by 0 days.

This patent is subject to a terminal disclaimer.

(21) Appl. No.: 18/650,932

(22) Filed: Apr. 30, 2024

(65) Prior Publication Data

US 2024/0293341 A1 Sep. 5, 2024

Related U.S. Application Data

(63) Continuation of application No. 17/438,316, filed as application No. PCT/EP2021/058518 on Mar. 31, 2021.

(30) Foreign Application Priority Data

Apr. 6, 2020 (FR) .................................... 2003425

(51) Int. Cl.
| | | |
|---|---|---|
| A61K 9/00 | (2006.01) | |
| A61K 9/06 | (2006.01) | |
| A61K 31/135 | (2006.01) | |
| A61K 47/10 | (2017.01) | |
| A61K 47/38 | (2006.01) | |

(52) U.S. Cl.
CPC .............. *A61K 31/135* (2013.01); *A61K 9/06* (2013.01); *A61K 47/10* (2013.01); *A61K 47/38* (2013.01)

(58) Field of Classification Search
CPC . A61K 9/06; A61K 9/00; A61K 47/38; A61K 47/10
See application file for complete search history.

(56) References Cited

U.S. PATENT DOCUMENTS

| | | |
|---|---|---|
| 12,005,034 B2 | 6/2024 | Greco |
| 2002/0028789 A1 | 3/2002 | Ford |
| 2004/0076648 A1 | 4/2004 | Williams et al. |
| 2004/0101582 A1 | 5/2004 | Wolicki |
| 2005/0209220 A1 | 9/2005 | Conforti |
| 2011/0065627 A1 | 3/2011 | Barathur et al. |
| 2013/0035362 A1 | 2/2013 | Demopulos et al. |
| 2020/0197326 A1 | 6/2020 | Greco |
| 2022/0304949 A1 | 9/2022 | Nicolas et al. |
| 2022/0387594 A1 | 12/2022 | Lallemand et al. |
| 2023/0103300 A1 | 4/2023 | Principe et al. |
| 2023/0103462 A1 | 4/2023 | Nicolas et al. |
| 2023/0201138 A1 | 6/2023 | Greco |
| 2024/0041766 A1 | 2/2024 | Lallemand et al. |

FOREIGN PATENT DOCUMENTS

| | | |
|---|---|---|
| CA | 2747845 | 10/2012 |
| CN | 110338191 | 10/2019 |
| EP | 3187174 | 7/2017 |
| EP | 3228634 | 10/2017 |
| FR | 3065371 | 10/2018 |
| WO | WO 03/015699 | 2/2003 |
| WO | WO 03/055475 | 7/2003 |
| WO | WO 2008/021847 | 2/2008 |
| WO | WO 2011/070318 | 6/2011 |
| WO | WO 2015/177288 | 11/2015 |
| WO | WO 2016/057789 | 4/2016 |
| WO | WO 2017/106714 | 6/2017 |
| WO | WO 2018/106107 | 6/2018 |
| WO | WO 2018/106108 | 6/2018 |
| WO | WO 2018/197307 | 11/2018 |
| WO | WO 2020/198252 | 10/2020 |

OTHER PUBLICATIONS

Kopsky et al. "High Doses of Topical Amitriptyline in Neuropathic Pain: Two Cases and Literature Review," Topical Amitriptyline in Neuropathic Pain, Jun. 2011, vol. 12, No. 2, pp. 148-153.
International Search Report with English Translation for PCT/EP2021/058518, mailed Jun. 29, 2021, 6 pages.
Barton et al. "A Double-Blind, Placebo-Controlled Trial of a Topical Treatment for Chemotherapy-Induced Peripheral Neuropathy: NCCTG Trial N06CA," Support Care Cancer, 2011, vol. 19, pp. 833-841.
Black et al. "Multiple Sodium Channel Isoforms and Mitogen-Activated Protein Kinases Are Present in Painful Human Neuromas," Annals of Neurology, 2008, vol. 64, pp. 644-653.
Fornasari "Pharmacotherapy for Neuropathic Pain: A Review," Pain, 2017, vol. 6, Supplement 1, pp. S25-233.
Gewandter et al. "A Phase III Randomized, Placebo-Controlled Study of Topical Amitriptyline and Ketamine for Chemotherapy-Induced Peripheral Neuropathy (CIPN): A University of Rochester CCOP Study of 462 Cancer Survivors," Support Care Cancer, 2014, vol. 22, pp. 1807-1814.
Kopsky et al. "Topical phenytoin for the treatment of neuropathic pain," Journal of Pain Research, Feb. 27, 2017, pp. 469-473.
Machado et al. "In vitro evaluation of the antibacterial activity of amitriptyline and its synergistic effect with ciprofloxacin, sulfamethoxazole-trimethoprim, and colistin as an alternative in drug repositioning," Medicinal Chemistry Research, 2020, vol. 29, No. 1, pp. 166-177.

(Continued)

*Primary Examiner* — Bruck Kifle
(74) *Attorney, Agent, or Firm* — Sheridan Ross P.C.

(57) ABSTRACT

The present invention relates to a topical pharmaceutical composition in the form of an aqueous gel comprising at least amitriptyline and/or a pharmaceutically acceptable salt thereof with a content between 10 and 30% by weight relative to the total weight of the composition, and water.

11 Claims, No Drawings

(56) References Cited

OTHER PUBLICATIONS

Mandal et al. "An Investigation on In Vitro and In Vivo Antimicrobial Properties of the Antidepressant: Amitriptyline Hydrochloride," Brazilian Journal of Microbiology, 2010, vol. 41, pp. 635-642.
Moore et al. "Amitriptyline for neuropathic pain in adults (Review)," Cochrane Database of Systematic Reviews, 2015, Issue 7, Art. No. CD008242, 53 pages.
Starabova et al. "Pathophysiology of Chemotherapy-Induced Peripheral Neuropathy," Frontiers in Molecular Neuroscience, May 2017, vol. 10, Article 174, 21 pages.
Su et al. "Amitriptyline Therapy in Chronic Pain," International Archives of Clinical Pharmacology, 2015, vol. 1, 5 pages.
Subedi et al. "Phantom Limb Pain: Mechanisms and Treatment Approaches," Pain Research and Treatment, 2011, vol. 2011, Article ID 864605, 8 pages.
Zelenka, M., et al. "Effect of amitriptyline on pain behavior in vincristine neuropathy," 33rd Annual Meeting of the Society of Neuroscience (New Orleans, LA, USA), Nov. 8-12, 2003, 1 page.
Zelman "Stabilizers, Thickeners and Gelling Agents," Food & Nutrition Magazine, May 2, 2017, 4 pages [retrieved online from: foodandnutrition.org/may-june-2017/stabilizers-thickeners-gelling-agents].

TOPICAL PHARMACEUTICAL COMPOSITION IN THE FORM OF AQUEOUS GEL COMPRISING AT LEAST AMITRIPTYLINE

CROSS-REFERENCE TO RELATED APPLICATIONS

This application is a continuation of U.S. patent application Ser. No. 17/438,316, filed Sep. 10, 2021, which is a national stage application under 35 U.S.C. 371 and claims the benefit of PCT Application No. PCT/EP2021/058518 having an international filing date of 31 Mar. 2021, which designated the United States, which PCT application claimed the benefit of French Patent Application No. FR2003425 filed 6 Apr. 2020, the disclosures of each of which are incorporated herein by reference in their entireties.

The present invention relates to a topical pharmaceutical composition in the form of aqueous gel comprising at least amitriptyline and/or a pharmaceutically acceptable salt thereof, in a content between 10 and 30% by weight relative to the total weight of the composition, and water.

Peripheral neuropathic pain is caused by damage to the nerve structures such as peripheral nerve endings or the nociceptors which become extremely sensitive to stimulation and can generate impulses in the absence of stimulation.

This damage can be caused by many reasons such as trauma, diseases such as diabetes, shingles and advanced cancers, chemotherapy treatments or chemical burns. Peripheral nerve damage can lead to pathological conditions characterised by the presence of continuous spontaneous superficial pain (burning or painful cold sensation) or deep pain (compression or vice-like sensation), paroxysmal pain (electric shocks, stabbing pain) with hypoesthesia or on the contrary hyperalgesia (increased response to harmful stimuli) on clinical examination, allodynia (pain caused by non-painful stimulus) or even hyperpathia (persistent pain on repeated stimulation that is not normally nociceptive). Neuropathies may also be associated with sensory signs such as paraesthesia, numbness, pruritus.

Chemotherapy-induced neuropathies are particularly common, disabling and difficult to treat. They are dose-dependent. Peripheral nerve damage represents the majority of neurological damage related to chemotherapy toxicity. They are the consequence of a direct toxic damage to the axon or demyelination and represent the most frequent limiting factor after haematological toxicity.

Thus, in the event of chemotherapy-induced neuropathies, the doses of chemotherapy will be reduced or the treatment may be stopped, which represents a real loss of opportunity for the patient.

Thus neuropathies have been observed following treatment with alkaloids (vincristine vinblastine, vinorelbine), often involving small fibre damage, platinum derivatives (oxaliplatin, cisplatin, carboplatin), anti-topoisomerase (VP16), proteasome inhibitors (bortezomib, carfilzomib), thalidomide derivatives such as lenalidomide, taxanes such as taxol or taxotere more likely to affect the large fibres. There are also neuropathies after immunotherapeutic treatment such as for example anti-CD20, anti-CD30, anti-CD38.

These chemotherapy-induced pains act according to mechanisms that are not well known, and some authors believe that they are caused by direct toxic damage to the sensory axon, to demyelination or also an alteration of the calcium metabolism linked to damage to the mitochondria, the site of action of paclitaxel and vincristine, for example.

Thus it is known that taxanes are involved in spinal ganglia, microtubules, mitochondria and nerve endings, platinum salts are involved in myelin and ion channels whereas alkaloids are involved in myelin and microtubules.

These neuropathic pains are often refractory to the usual analgesic treatments and lead to reductions in the dose or even the discontinuation of chemotherapy. Currently they are managed by per os treatments comprising antidepressants (amitriptyline, duloxetine, venlafaxine, etc.) and/or antiepileptics (gabapentin, pregabalin). Unfortunately, these systemic treatments cause major side effects (dizziness, drowsiness, memory loss, dry mouth or even urine retention, nausea, etc.) leading to poor compliance and unsatisfactory pain control.

These pains affect mainly the extremities of the hands and feed and lead to a considerable change to the quality of life of patients with functional impotence which can extend to not being to walk, difficulties gripping, altered sleep, the appearance of a depression syndrome or even suicidal tendencies. There can also be very significant impact on social and professional life.

The intensity of the pain is often described as severe in patients who rate their pain as more than 7/10 on the Simple Numerical Scale (pain rated from 0 to 10).

Post-herpetic neuropathies, have a different origin and are generally linked to nerve damage caused by a previous infection by the herpes zoster virus. The damaged nerves are no longer capable of correctly transmitting the signals from the skin to the brain.

Tricyclic antidepressants are chemical compounds that were discovered at the beginning of the 1950s. They are used widely for treating various mental disorders, in particular depression, panic attacks, obsessive-compulsive disorder, enuresis in children, bipolar disorder and hyperactivity. They are also used as analgesics.

These compounds are generally administered orally.

Amitriptyline is a tricyclic antidepressant discovered in 1960 which has been frequently recommended as a first-line treatment for major depression, post-traumatic stress disorder (PTSD), generalised anxiety disorder (GAD), social phobia (SP), panic disorder, fibromyalgia, chronic musculoskeletal pain, akinesia in Parkinson's disease, cataplexy, migraines, Parkinson's disease, vasomotor symptoms of menopause, nocturnal enuresis, premenstrual dysphoric disorder (PMDD), bipolar disorder, bulimia nervosa, obsessive-compulsive disorder (OCD) and neuropathic pain.

In the past, patients were generally treated by analgesics for pain relief. Oral administration was largely preferred.

However, the oral administration of amitriptyline, as with all tricyclic antidepressants, has a number of side effects associated with their anti-cholinergic effects (risk of arterial hypotension, sinus or supra-ventricular tachycardia, rarely VAD, blurred vision, dry mouth, skin flushes, acute retention of urine or slowed transit), anti-alpha adrenergic (risk of sedation, hypotension, impotence), central inhibitors of sympathetic reflexes or even membrane stabilisers (pro-arrhythmogenic effect). In particular, one of the worse and dreaded effects of amitriptyline is QT prolongation which can lead to the death of a patient who has not been properly monitored.

In particular, when amitriptyline is administered orally for the treatment of diabetic neuropathic pain, cases of sedation, orthostatic hypotension and anti-cholinergic effects have been reported (see in particular Kiani et al, Iran J Pharm. Res. 2015 Fall; 14(4):1263-8). In the long term, patients report memory problems, difficulties concentrating with a significant effect on the quality of their work or their daily life.

Furthermore, the efficacy of amitriptyline taken orally is slow (5 to 7 days of treatment are needed to begin to appreciate the efficacy of the product), and varies according to the patient and is incomplete. It is therefore often necessary to use combinations of analgesics to overcome these drawbacks.

Additionally, oral tricyclic antidepressants often have a bad reputation with patients because of their use for different mental disorders.

Given the problems of oral treatments, attempts have been made to provide topical treatments. The efficacy of topical amitriptyline for neuropathic pain has not been demonstrated. In particular, the article of Thomson et al "*Systematic review of topical amitriptyline for the treatment of neuropathic pain*", J. Clin. Pharm. Therm. 2015, 40, 496-503, concludes that controlled clinical trials show that topical amitriptyline is not effective for the treatment of neuropathic pain. The maximum dose used is 5% for a patient suffering multiple sclerosis and suffering neuropathic pain. Also, the article "*A phase III randomized, placebo-controlled study of topical amitriptyline and ketamine for chemotherapy-induced peripherical neuropathy*", Support Care Cancer, 2014 July; 22(7):1807-1814, concluded that a topical composition comprising 2% by weight ketamine and 4% by weight amitriptyline was not effective for treating post-chemotherapy neuropathic pain.

Thus, there is no satisfactory treatment for neuropathic pain, induced in particular by chemotherapy. Furthermore, treatments combining ketamine and amitriptyline which appeared to be successful in patients with post-herpetic or diabetic neuropathic pain, have not been able to cure neuropathic pain induced by chemotherapy, as reported in the aforementioned phase III clinical trial.

In addition, the doses considered, despite the disabling nature of these pains have never exceeded 5% either orally or topically.

Furthermore, patients suffering neuropathy in the extremities (feet and hands) often have damaged or chapped and dry skin.

In parallel, international application WO 2018/197307 previously filed by Algotherapeutix, as well as the article "Rossignol, J. and al. High concentration of topical amitriptyline for treating chemotherapy-induced neuropathies. *Support Care Cancer* 27, 3053-3059 (2019)" demonstrated the efficacy of a pharmaceutic composition in cream form comprising 10 to 30% by weight amitriptyline for topical use in the treatment of peripheral neuropathic pain. Creams are the most commonly use dosage form for the topical administration of active ingredients as they generally provide better transdermal uptake and good solubilisation of all active ingredients. However, the physico-chemical stability of the composition according to application WO 2018/197307 in the form of cream and more precisely in the form of an oil-in-water emulsion, is not satisfactory, in particular for use as a drug.

Amitriptyline hydrochloride is an amphiphilic molecule which is soluble in water as a salt. It was discovered surprisingly that the presence of these electrolytes is destabilising for oil-in-water emulsions, by masking the surface changes of the oil globules and by disrupting the oil/water interface equilibrium. This destabilisation caused a phase shift in the emulsion and eventually a total separation of the oil and water. At the same time, a chemical reaction occurs, resulting in the yellowing of the initially white colour of the emulsion. This phase shift and yellowing are problematic for the possible entry onto the market of the composition, in particular as a drug.

There is therefore a real need to provide an amitriptyline-based composition that is stable over time and effective as a skin application in the treatment of pain, in particular in the treatment of peripheral neuropathies and in particular neuropathies induced by chemotherapy.

It has been discovered in a surprising manner that a pharmaceutical composition in the form of aqueous gel for a topical application comprising (i) at least amitriptyline and/or a pharmaceutically acceptable salt thereof, in which the total content of amitriptyline and/or a pharmaceutically acceptable salt thereof is between 10 and 30% by weight relative to the total weight of the composition, and (ii) water, was particularly stable over time and enabled the effective treatment of pain, in particular chemotherapy-induced peripheral neuropathic (or CIPN) pain, post-herpetic neuropathic (or PHN) pain or also diabetic peripheral neuropathic (or DPN) pain.

The invention thus relates to a pharmaceutical composition in the form of an aqueous gel for a topical application comprising (i) at least amitriptyline and/or a pharmaceutically acceptable salt thereof, in which the total content of amitriptyline and/or a pharmaceutically acceptable salt thereof is between 10 and 30% by weight relative to the total weight of the composition, and (ii) water.

In particular, the composition according to the invention has good stability over time at ambient temperature (25° C.) but also at higher storage temperatures (45° C. for example).

It has also been found that the pharmaceutical composition in the form of an aqueous gel according to the invention facilitates the penetration of amitriptyline through the skin, and thus achieves good therapeutic efficacy.

The composition according to the invention also has improved bioavailability, preferably at concentrations of amitriptyline and/or a pharmaceutically acceptable salt thereof of 10 to 25% by weight and in particular between 10 and 20% by weight relative to the total weight of the composition. Indeed, at high concentrations amitriptyline tends to rearrange itself, leading to the formation of aggregates likely to limit the bioavailability.

In addition, the composition according to the invention comprises few excipients, which promotes a good local tolerance of the composition (less risk of allergy, less risk of irritation).

The composition according to the invention also has good usage properties, namely the composition is translucent, odourless and pleasant to touch. In particular, the composition according to the invention has a non-greasy feel compared to the emulsions disclosed in application WO2018/197307.

Furthermore, the composition according to the invention is very easily administered in pump bottles, unlike oil-in-water emulsions. These pump bottles are particularly useful for ensuring good reproducibility and accuracy of the administered dose of active ingredient.

It has also been found, in a particularly surprising manner, that the pharmaceutical composition in the form of an aqueous gel for a topical application according to the invention, was effective in treating erythromelalgia.

Erythromelalgia is an uncommon episodic acrosyndrome affecting mainly both lower limbs symmetrically with erythema, heat and burning pain. Many scientific articles describe this orphan disease, in particular "Leroux M B. Erythromelalgia: a cutaneous manifestation of neuropathy? *An Bras Dermatol.* 2018; 93(1): 86-94".

The topical application (via the skin) of the composition according to the invention results in an effective treatment of erythromelalgia and of neuropathic pain, more particularly peripheral neuropathic pain such as chemotherapy-induced peripheral neuropathic, post-herpetic and diabetic pain.

It has been found that a composition based on amitriptyline not only alleviates pain but also makes the skin healthier.

Furthermore, the topical application of the composition according to the invention has few, if any side effects. In particular, no skin irritations have been observed at the application side of the composition.

The invention also relates to the composition according to the invention for use as a drug, and more particularly for topical use in the treatment of neuropathic pain such as peripheral neuropathic pain.

Other objects, features, aspects and advantages of the invention are described more clearly in the following and by way of the following example.

In the present description, and unless otherwise indicated:
the expression "at least one" is equivalent to the expression "one or more" and can be substituted for the latter;
the expression "is between . . . and . . . " is equivalent to the expression "from . . . to . . . " and can be substituted for the latter, and implies that the limits are included;
the expression "polyoxyalkylenated" corresponds, within the meaning of the invention, to a motif —(O-alkyl)$_n$-, where n is an integer varying from 2 to 200, preferably 2 to 40, more preferably 2 to 20;
the expression "polyoxyethylenated" corresponds, within the meaning of the invention, to a motif —(O—CH$_2$CH$_2$)$_n$—, where n is an integer varying from 2 to 200, preferably from 2 to 40, more preferably from 2 to 20.

The pharmaceutical composition according to the invention is in the form of an aqueous gel.

According to the Clinical Data Interchange Standards Consortium (CDISC), a pharmaceutical gel is a semi-solid dosage form containing a gelling agent to give rigidity to a solution or a colloidal dispersion. A gel may contain suspended particles.

Within the meaning of the invention, the compositions in the form of gel according to the invention comprise viscous aqueous compositions with a viscosity between 400 and 2500 mPa·s (at a temperature of 20° C. and at atmospheric pressure).

Preferably, the viscosity of compositions in the form of aqueous gel according to the invention, at a temperature of 20° C. and at atmospheric pressure, is between 400 and 2500 mPa·s; more preferably between 900 and 2000 mPa·s; and even more preferably between 1000 and 1500 mPa·s.

By way of example, the viscosity of aqueous gel compositions according to the invention is determined by means of a Brookfield LV viscometer, using the mobile number 63, rotating at a speed of 50 rpm (revolutions per minute), at a temperature 20.0° C.+/−2.0° C.) in a 30 mL container, 40 mm high and 35 mm in diameter. When the viscometer is calibrated, the mobile is immersed in the gel up to one centimetre from the bottom of the bottle. The viscosity is taken when the measurement is stable.

The composition according to the invention is not in the form of an emulsion, such as an oil-in-water emulsion or a water-in-oil emulsion. In other words, the composition according to the invention does not comprises an oil phase.

The composition according to the invention is therefore not in the form of cream.

Advantageously, the composition according to the invention is free of fatty substance. Within the meaning of the invention, a "fatty substance", is an organic compound which is insoluble in water at 25° C. and at atmospheric pressure (760 mm Hg, i.e. 1.013.10$^5$ Pa), i.e. with a solubility in water of less than 5% and preferably less than 1%, still more preferably less than 0.10%. Examples of fatty substances can include waxes, hydrocarbons, fatty alcohols comprising 9 to 40 carbon atoms, fatty esters comprising 9 to 40 carbon atoms, fatty ethers comprising preferably 9 to 40 carbon atoms, silicones and mixtures thereof.

Amitriptyline

The composition according to the present invention comprises at least amitriptyline and/or a pharmaceutically acceptable salt thereof.

According to the invention, the total content of amitriptyline and/or a pharmaceutically acceptable salt thereof is between 10 and 30% by weight relative to the total weight of the composition.

The amitriptyline has the following formula (I):

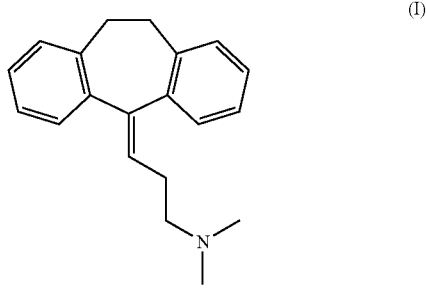 [SMILES: CN(C)CCC=C1c2ccccc2CCc2ccccc21]

(I)

In the context of the present invention, "pharmaceutically acceptable salts of amitriptyline" means salts that are compatible with a pharmaceutical composition, i.e. intended for administration to humans. In particular, pharmaceutically acceptable salts of amitriptyline are hydrates, solvates, acid salts such as hydrochlorides and amitriptyline clathrates.

The most preferred salt of amitriptyline, is amitriptyline hydrochloride.

Preferably, the total content of amitriptyline and/or a pharmaceutically acceptable salt thereof is between 10 and 25% by weight, more preferably between 10 and 20% by weight, even more preferably between 10 and 15% by weight, relative to the total weight of the composition.

More preferably, the total content of amitriptyline hydrochloride is between 10 and 25% by weight, even more preferably between 10 and 20% by weight, better still between 10 and 15% by weight, relative to total weight of the composition.

In particular, it was observed in a surprising manner that when the total content of amitriptyline, and/or a pharmaceutically acceptable salt thereof such as amitriptyline hydrochloride, is between 10 and 25% by weight, more preferably between 10 and 20% by weight, relative to the total weight of the composition according to the invention, then the bioavailability of amitriptyline of the composition according to the invention is significantly improved.

Indeed, it has been observed that a high concentration of amitriptyline tends to rearrange itself, leading to the formation of aggregates that may limit the bioavailability.

Water

The composition according to the present invention comprises water.

Preferably, the total content of water is greater than or equal to 65% by weight, more preferably between 65 and 90% by weight; even more preferably between 70 and 90% by weight, better still between 75 and 85% by weight, relative to total weight of the composition.

Cellulosic Polymers

Preferably, the composition according to the invention comprises at least one cellulosic polymer.

A "cellulosic" polymer according to the invention means any polysaccharide compound, substituted or not, having in its structure chains of glucose residues linked by β-1,4 bonds; in addition to unsubstituted celluloses, cellulose derivatives may be anionic, cationic, amphoteric or non-ionic.

Thus the cellulosic polymers which can be used according to the invention can be selected from unsubstituted celluloses, including a microcrystalline form and substituted celluloses.

More preferably, the cellulosic polymers which can be used according to the invention do not comprise a $C_{10}$-$C_{30}$ fatty side chain in their structure.

Preferably, the cellulosic polymer(s) which can be used according to the invention have an average molecular weight between 5 000 and 1 500 000, more preferably between 50 000 and 800 000, even more preferably between 400 000 and 800 000.

Among the cellulosic polymers according to the invention, a distinction can be made between cellulose ethers, cellulose esters and cellulose ester ethers.

Cellulose esters include inorganic cellulose esters (nitrates, cellulose sulphates or phosphates, etc.), organic cellulose esters (cellulose monoacetates, triacetates, amidopropionates, acetatebutyrates, acetatepropionates or acetatetrimellitates, etc.) and mixed organic/inorganic cellulose esters such as cellulose acetatebutyrate sulphates and cellulose acetatepropionate sulphates. Cellulose ether esters include hydroxypropylmethylcellulose phtalates and ethyl cellulose sulphates.

The non-ionic cellulose ethers can include ($C_1$-$C_4$)alkylcelluloses such as methylcelluloses and ethylcelluloses (for example Ethocel standard 100 Premium of DOW CHEMICAL); (poly)hydroxy($C_1$-$C_4$)alkylcelluloses such as hydroxymethylcelluloses, hydroxyethylcelluloses (for example Natrosol 250 HHR offered by AQUALON) and hydroxypropylcelluloses (for example Klucel EF of AQUALON); mixed celluloses (poly)hydroxy($C_1$-$C_4$)alkyl-($C_1$-$C_4$)alkylcelluloses such as hydroxypropyl-methylcelluloses (for example Methocel E4M of DOW CHEMICAL), hydroxyethyl-methylcelluloses, hydroxyethyl-ethylcelluloses (for example Bermocoll E 481 FQ of AKZO NOBEL) and hydroxybutyl-methylcelluloses.

The anionic cellulose ethers can include (poly)carboxy($C_1$-$C_4$)alkylcelluloses and salts thereof. This can include by way of example carboxymethylcelluloses, carboxymethylmethylcelluloses (for example Blanose 7M of the company AQUALON) and carboxymethylhydroxyethylcelluloses and their sodium salts.

The cationic cellulose ethers can include derivatives of cationic cellulose such as cellulose copolymers or derivatives of cellulose grafted with a water-soluble quaternary ammonium monomer, and described in particular in U.S. Pat. No. 4,131,576, such as (poly)hydroxy($C_1$-$C_4$)alkylcelluloses, such as grafted hydroxymethyl-, hydroxyethyl- or hydroxypropylcelluloses in particular with a salt of methacryloylethyl-trimethylammonium, methacrylmidopropyl-trimethylammonium, dimethyl-diallylammonium. The products marketed with this definition are more particularly products sold with the name "Celquat® L200" and "Celquat® H 100" by the company National Starch.

According to a preferred embodiment of the invention, the cellulosic polymer(s) are selected from cellulosic polymers do not include a $C_{10}$-$C_{30}$ fatty side chain in their structure; more preferably from cellulose ethers; even more preferably from non-ionic cellulose ethers; better still from (a) ($C_1$-$C_4$)alkylcelluloses such as methylcelluloses and ethylcelluloses, (b) (poly)hydroxy($C_1$-$C_4$)alkylcelluloses such as hydroxymethylcelluloses, hydroxyethylcelluloses and hydroxypropylcelluloses, (c) mixed celluloses (poly)hydroxy($C_1$-$C_4$)alkyl-($C_1$-$C_4$)alkylcelluloses such as hydroxypropyl-methylcelluloses, hydroxypropyl-ethylcelluloses, hydroxyethyl-methylcelluloses, hydroxyethyl-ethylcelluloses and hydroxybutyl-methylcelluloses, and (d) mixtures thereof.

More preferably, the composition according to the invention comprises at least one (poly)hydroxy($C_1$-$C_4$)alkylcellulose such as hydroxymethylcelluloses, hydroxyethylcelluloses and hydroxypropylcelluloses; better still at least hydroxyethyl cellulose.

Preferably, when the composition according to the invention comprises at least one cellulosic polymer, the total content of cellulosic polymer(s) is between 0.1 and 10% by weight, more preferably between 0.5 and 5% by weight, even more preferably between 1 and 2.5% by weight, relative to the total weight of the composition.

Preferably, when the composition according to the invention comprises at least one cellulosic polymer, the total content of (poly)hydroxy($C_1$-$C_4$)alkylcellulose(s) is between 0.1 and 10% by weight, more preferably between 0.5 and 5% by weight, even more preferably between 1 and 2.5% by weight, relative to the total weight of the composition.

Preferably, when the composition according to the invention comprises at least one cellulosic polymer, the total content of hydroxyethyl cellulose is between 0.1 and 10% by weight, more preferably between 0.5 and 5% by weight, even more preferably between 1 and 2.5% by weight, relative to the total weight of the composition.

Polyols

Preferably, the composition according to the present invention comprises at least a $C_2$-$C_8$ polyol.

A "$C_2$-$C_8$ polyol" within the meaning of the present invention, is an organic compound consisting of $C_2$-$C_8$ hydrocarbon chain, optionally interrupted by one or more oxygen atoms, and carrying at least two free hydroxyl groups (—OH) carried by different carbon atoms, this compound may be cyclic or acyclic, linear or branched, saturated or unsaturated, and in the liquid state at ambient temperature (25° C.) and atmospheric pressure ($1.013.10^5$ Pa).

Preferably, the $C_2$-$C_8$ polyol(s) according to the invention are acyclic and non-aromatic.

The $C_2$-$C_8$ polyols according to the invention comprise in their structure of 2 to 8 carbon atoms, preferably 2 to 6 carbon atoms, more preferably 2 to 5 carbon atoms.

More particularly, the polyol or polyols used according to the invention comprise 2 to 10 hydroxy groups, more preferably 2 to 5 hydroxy groups, even more preferably 2 to 3 hydroxy groups.

In a preferred manner, the $C_2$-$C_8$ polyol(s) used according to the invention are selected from $C_3$-$C_6$ polyols, ethylene glycol, and mixtures thereof.

According to a preferred embodiment of the invention, the $C_2$-$C_8$ polyol(s) used according to the invention are selected from propylene glycol, 1,3-propanediol, 1,3-butylene glycol, pentane-1,2-diol, dipropylene glycol, hexylene glycol, pentylene glycol, glycerol, ethylene glycol, and a mixture of these compounds; more preferably the composition comprises at least propylene glycol.

Preferably, when the composition according to the invention comprises at least one $C_2$-$C_8$ polyol, the total content of $C_2$-$C_8$ polyol(s) is between 0.1 and 15% by weight, more preferably between 0.5 and 10% by weight, even more preferably between 1 and 6% by weight, and better still between 3 and 6% by weight, relative to the total weight of the composition.

Preferably, when a composition according to the invention comprises at least one $C_2$-$C_8$ polyol, the total content of propylene glycol is between 0.1 and 15% by weight, more preferably between 0.5 and 10% by weight, even more preferably between 1 and 6% by weight, and better still between 3 and 6% by weight, relative to the total weight of the composition.

Preferably, when the composition according to the invention comprises at least one cellulosic polymer and at least one $C_2$-$C_8$ polyol, the weight ratio of the total content of $C_2$-$C_8$ polyol(s) on the one hand to the total content of cellulosic polymer(s) on the other hand, ranges from 0.01 to 150, more preferably from 0.1 to 20, even more preferably from 0.4 to 6, more preferably from 1 to 6, even from 1.2 to 6.

Advantageously, when the composition according to the invention comprises at least one cellulosic polymer and at least one $C_2$-$C_8$ polyol, the total content by weight of cellulosic polymer(s) is strictly lower than the total content by weight of $C_2$-$C_8$ polyol(s).

Surfactants

The composition according to the present invention may optionally comprise at least one surfactant.

The surfactants that can be used according to the invention can be selected from anionic surfactants, cationic surfactants, amphoteric surfactants and/or zwitterionic surfactants, non-ionic surfactants, and mixtures thereof.

More preferably, the surfactant(s) that can be used according to the invention are selected from non-ionic surfactants.

Non-ionic surfactants that can be used according to the invention can be selected from alkyl polyglucosides (APG), oxyalkylenated glycerol esters, oxyalkylenated fatty acid and sorbitan esters, polyoxyalkylenated fatty acid esters (in particular polyoxyethylenated and/or polyoxypropylenated) optionally in association with a fatty acid and glycerol ester such as the mixture PEG-100 Stearate/Glyceryl Stearate available for example from the company ICI under the name Arlacel 165, oxyalkylenated sugar esters, and mixtures thereof.

Alkylpolyglucosides can include those containing an alkyl group comprising 6 to 30 carbon atoms and preferably 8 to 16 carbon atoms, and containing a glucoside group comprising preferably 1.2 to 3 units of glucoside. Alkylpolyglucosides can be selected for example from the decylglucoside (Alkyl-$C_9$/$C_{11}$-polyglucoside (1.4)) such as the product available under the name Mydol 10® from the company Kao Chemicals or the product available under the name Plantacare 2000 UP® from the company Cognis; the caprylyl/capryl glucoside such as the product available under the name Plantacare KE 3711® from the company Cognis; lauryl glucoside such as the product available under the name Plantacare 1200 UP® from the company Cognis; cocoglucoside such as the product available under the name Plantacare 818 UP® from the company Cognis; caprylylglucoside such as the product available under the name Plantacare 810 UP® from the company Cognis; and mixtures thereof.

Oxyalkylenated glycerol esters include in particular polyoxyethylenated derivatives of glyceryl and fatty acid esters and hydrogenated derivatives thereof. These oxyalkylenated glycerol esters can be selected for example from hydrogenated and oxyethylenated glyceryl and fatty acid esters such as PEG-200 hydrogenated glyceryl palmate available under the name Rewoderm LI-S 80 from the company Goldschmidt; oxyethylenated glyceryl cocoates such as PEG-7 glyceryl cocoate available under the name Tegosoft GC from the company Goldschmidt, and PEG-30 glyceryl cocoate available under the name Rewoderm LI-63 from the company Goldschmidt; oxyethylenated glyceryl stearates; and mixtures thereof.

Esters of oxyalkylenated sugars are in particular polyethylene glycol ethers of fatty acid and sugar esters. These oxyalkylenated sugar esters can be selected for example from oxyethylenated glucose esters such as PEG-120 methyl glucose dioleate available under the name Glucamate DOE 120 from the company Amerchol.

Preferably, the number of moles of alkylene oxide of the non-ionic surfactants used according to the invention varies from 2 to 400; more preferably from 4 to 250.

Preferably, the composition according to the invention is free of surfactant.

According to a particular embodiment of the invention, the composition comprises at least one non-ionic surfactant; more preferably a non-ionic surfactant selected from polyoxyalkylenated glycerol esters; even more preferably at least one non-ionic surfactant selected from glyceryl esters and hydrogenated and polyoxyethylenated fatty acids such as PEG-200 hydrogenated glyceryl palmate, polyoxyethylenated glyceryl cocoates such as PEG-7 glyceryl cocoate and PEG-30 glyceryl cocoate, polyoxyethylenated glyceryl stearates, and mixtures thereof.

Even more preferably according to this embodiment, the composition according to the invention comprises at least one polyoxyethylenated glyceryl cocate.

Preferably, when the composition according to the invention comprises at least one surfactant, the total content of surfactant(s) is between 0.1 and 10% by weight, more preferably between 0.5 and 5% by weight, even more preferably between 1 and 4% by weight, relative to the total weight of the composition.

Preferably, when the composition according to the invention comprises at least one surfactant, the total content of non-ionic surfactant(s) is between 0.1 and 10% by weight, more preferably between 0.5 and 5% by weight, even more preferably between 1 and 4% by weight, relative to the total weight of the composition.

Preferably, when the composition according to the invention comprises at least one surfactant, the total content of (poly)oxyalkylenated glycerol ester(s) is between 0.1 and 10% by weight, more preferably between 0.5 and 5% by weight, even more preferably between 1 and 4% by weight, relative to the total weight of the composition.

According to a preferred embodiment of the invention, the composition is free of anti-oxidant agent.

According to a variant of the invention, the composition further comprises at least one anti-oxidant agent; more preferably selected from tocopherol and the esters thereof, such as tocopherol acetate, propyl gallate, butylated hydroxytoluene (BHT), butylated hydroxyanisole (BHA), and mixtures thereof.

According to a preferred embodiment of the invention, the composition is free of sequestering agent.

According to one variant of the invention, the composition further comprises at least one sequestering agent; more preferably selected from (a) ethylenediaminetetraacetic acid (EDTA) and the salts thereof such as the disodium salt of ethylenediaminetetraacetic acid (Disodium EDTA), (b) phosphonic derivatives and the salts thereof such as hexamethylene diaminetetra(methylene phosphonic) acid, ethylenediamine tetra(methylene phosphonic) acid, 1-hydroxyethylidene-1,1-diphosphonic acid, aminotri(methylene phosphonic) acid, diethylene-triamine penta(methylene phosphonic) acid, (c) polyaminated polymers such as polyalkylene polyamines and derivatives thereof, in particular polyethyleneimine, (d) dendrimers with chelating activity, (e) proteins such as spermine, spermidine, transferrin, ferritin, (f) carboxylic acids such as phytic acid, citric acid, malic acid, nitrilo-acetic acid, fumaric acid, tartaric acid, succinic acid, oxalic acid, (g) desferrioxamine mesylate, and mixtures thereof.

The definition of "sequestering agent" (also referred to as "chelating agent") is well known to the person skilled in the art and refers to a compound or a mixture of compounds capable of forming a chelate with a metal ion. A chelate is an inorganic complex in which a compound (the sequestering or chelating agent) is coordinated with a metal ion, i.e. it forms one or more bonds with the metal ion (formation of a cycle including the metal ion).

A sequestering (or chelating) agent generally comprises at least two electron-donor atoms that enable the formation of bonds with the metal ion.

According to another particular embodiment of the invention, the composition comprises at least one sequestering agent and at least one anti-oxidant agent.

According to another variant of the invention, the composition is free of fatty substance, sequestering agent and/or anti-oxidant agent.

Preferably, the pH of the composition according to the invention is between 3 and 8, more preferably between 4 and 7, and better still between 5 and 6.

The pH of these compositions can be adjusted to the desired value by means of alkalising agents or acidifying agents usually used. Examples of alkalising agents can include ammonia, alkanolamines, mineral or organic hydroxides. The acidifying agents can include for example mineral or organic acids such as hydrochloric acid, orthophosphoric acid, carboxylic acids such as for example acetic acid, tartaric acid, citric acid, lactic acid, sulphonic acids.

The composition according to the invention may also contain additives usually used in pharmaceuticals, such as one or more fragrances, buffers, dyes, antibacterial and/or antifungal agents.

As an antibacterial, parabens are preferably used, and more preferably methylparaben.

These additives may be present in the composition according to the invention in a quantity from 0 to 20% by weight relative to the total weight of the composition.

The person skilled in the art will take care to choose these optional additives and their quantities in such a way that they are not detrimental to the proprieties of the compositions of the present invention.

In a particularly preferred embodiment of the invention, the pharmaceutical composition in the form of an aqueous gel for topical application comprises:
  10 to 30% by weight, preferably 10 to 25% by weight, more preferably 10 to 20% by weight, even more preferably 10 to 15% by weight, amitriptyline or a pharmaceutically acceptable salt thereof, relative to the total weight of the composition,
  0.1 to 10% by weight, preferably 0.5 to 5% by weight, even more preferably 1 to 2.5% by weight, of at least one cellulosic polymer as described above, relative to the total weight of the composition,
  0.1 to 15% by weight, preferably 0.5 to 10% by weight, even more preferably 1 to 6% by weight, and better still 3 to 6% by weight, of at least one $C_2$-$C_8$ polyol as described above, relative to the total weight of the composition,
  optionally 0.1 to 10% by weight, more preferably 0.5 to 5% by weight, even more preferably 1 to 4% by weight, of at least one non-ionic surfactant as described above, relative to the total weight of the composition,
  optionally 0 to 3% by weight at least one sequestering agent and/or at least one anti-oxidant agent as described above,
  optionally 0 to 1% by weight of one or more pH adjusters as described above, so as to keep the pH between 3 and 8, preferably between 4 and 7, more preferably between 5 and 6,
  water, with a total content greater than or equal to 650% by weight, preferably between 65 and 90% by weight; more preferably between 70 and 90% by weight, even more preferably between 75 and 85% by weight, relative to the total weight of the composition.

According to one variant of this embodiment, the composition is free of fatty substance, surfactant, sequestering agent and/or anti-oxidant agent.

In a particularly preferred embodiment of the invention, the pharmaceutical composition in the form of an aqueous gel for topical application comprises:
  10 to 30% by weight, preferably 10 to 25% by weight, more preferably 10 to 20% by weight, even more preferably 10 to 15% by weight, amitriptyline or a pharmaceutically acceptable salt thereof, relative to the total weight of the composition,
  0.1 to 10% by weight, preferably 0.5 to 5% by weight, even more preferably 1 to 2.5% by weight, of at least one non-ionic cellulose ether, preferably of average molecular weight between 50 000 and 800 000, as described above, relative to the total weight of the composition,
  0.1 to 15% by weight, preferably 0.5 to 10% by weight, even more preferably 1 to 6% by weight, and better still 3 to 6% by weight, of at least one $C_2$-$C_8$ polyol selected from propylene glycol, 1,3-propanediol, 1,3-butylene glycol, pentane-1,2-diol, dipropylene glycol, hexylene glycol, pentylene glycol, glycerol, ethylene glycol, and a mixture of these compounds relative to the total weight of the composition,
  optionally 0.1 to 10% by weight, more preferably 0.5 to 5% by weight, even more preferably 1 to 4% by weight, of at least one oxyalkylenated glycerol ester as described above, relative to the total weight of the composition,
  optionally 0 to 3% by weight of at least one sequestering agent and/or at least one anti-oxidant agent as described above,
  optionally 0 to 1% by weight of one or more pH adjusters as described above, so as to keep the pH between 3 and 8, preferably between 4 and 7, more preferably between 5 and 6,
  water, in a total content greater than or equal to 65% by weight, preferably between 65 and 90% by weight; more preferably between 70 and 90% by weight, even more preferably between 75 and 85% by weight, relative to the total weight of the composition.

According to one variant of this embodiment, the composition is free of fatty substance, surfactant, sequestering agent and/or anti-oxidant agent.

The compositions according to these particularly preferred embodiments are particularly effective in the treatment of erythromelalgia and peripheral neuropathic pain, in particular chemotherapy-induced peripheral neuropathic pain.

These compositions according to this embodiment are particularly stable. These compositions were subjected to stability studies in ambient temperature (25° C.) and accelerated temperature (40° C.) conditions for 6 months. The result of these studies is that these compositions did not change in appearance or chemically (dosage of active ingredient and degradation products).

A preferred composition according to the invention was also subjected to forced degradation under strong acidity, strong alkalinity, heat, light and oxidative conditions. The observed degradation products remained within acceptable limits.

The subject-matter of the invention is also a composition according to the invention as described above for use as a drug.

The subject-matter of the invention is also a composition according to the invention as described above for topical use in the treatment of neuropathic pain; preferably for topical use in the treatment of peripheral neuropathic pain; more preferably for topical use in the treatment of chemotherapy-induced peripheral neuropathic pain, post-herpetic neuropathic pain, diabetic neuropathic pain; even more preferably for topical use in the treatment of chemotherapy-induced peripheral neuropathic pain.

The subject-matter of the invention is also a composition according to the invention as described above for topical use in the treatment of erythromelalgia.

The invention also relates to a composition according to the invention as described above for use in the treatment of cancers including chemotherapy sessions, the composition being administered topically between chemotherapy sessions for curing or preventing neuropathic pain, in particular peripheral pain, which may be induced by the chemotherapy.

The invention also relates to a composition according to the invention as described above for use in curing or preventing neuropathic pain, in particular peripheral pain, which may be induced by chemotherapy.

The following examples illustrate the composition according to the invention and the advantages of this composition. However, they do not represent a limitation of the present invention but simply illustrate the invention.

EXAMPLES

Example 1

Comparative ex vivo study of the percutaneous absorption of amitriptyline in a formulation A in the form of an aqueous gel (invention) and a formulation B in the form of cream (comparative).

The following aqueous gel (composition A) was prepared from the ingredients listed in the following table, the quantities being expressed in % by weight.

TABLE 1

| COMPOSITION A (Invention) | Quantity |
| --- | --- |
| Amitriptyline hydrochloride | 10 |
| Hydroxyethylcellulose | 1 |
| Propylene glycol | 5 |

TABLE 1-continued

| COMPOSITION A (Invention) | Quantity |
| --- | --- |
| PEG-7 glyceryl cocoate | 2 |
| Disodium salt of ethylenediaminetetraacetic acid | 0.1 |
| Propyl gallate | 0.05 |
| pH agent | Qs pH 5.5 ± 0.5 |
| Water | Qs 100 |

Composition B (cream) comprises 10% by weight amitriptyline hydrochloride and 90% by weight Excipial Hydrocreme®, available from the company Galderma, relative to the total weight of composition B.

Each of compositions A and B was applied to distinct samples of human skin. For each composition, the experiment was repeated 3 times with 3 skin samples from 3 different donors, giving 9 samples.

The skin samples are placed in a Frantz cell and heated to a surface temperature of 32° C.±1° C.

Composition A or B is spread homogenously with a spatula onto each skin sample at a rate of 10 mg per cell, corresponding to 5 mg/cm² skin.

The skin samples are rinsed 16 hours after application.

Each skin sample was placed using tweezers onto absorbent paper (dermis side down).

The stratum corneum was removed using adhesive strips.

After the removal of the stratum corneum the sample was perforated. The epidermis is then separated from the dermis. Each of them is placed in separate vials.

Different samples were then extracted.

This penetration profile was shown to be clinically effective in the study described in the aforementioned article by Rossignol et al.

The results of these extractions are summarised in the table below.

TABLE 2

|  | Composition A (Invention) | Composition B (Comparative) |
| --- | --- | --- |
| Concentration of amitriptyline resting on the surface of the skin - stratum corneum (µg) | 2.4 ± 1.5 | 3.3 ± 1.6 |
| Concentration of amitriptyline in the epidermis (µg) | 3.6 ± 2.6 | 4.1 ± 2.5 |
| Concentration of amitriptyline in the dermis (µg) | 5.2 ± 2.5 | 4.4 ± 2.2 |
| Concentration of amitriptyline in the receptor fluid (blood circulation) | 0.15 ± 0.08 | 0.13 ± 0.13 |
| Bioavailability (µg/cm² skin) | 9.0 ± 4.8 | 8.7 ± 4.0 |

It was also observed that the systemic passage of amitriptyline was less than 0.10% of the administered dose. This means that the systemic uptake of amitriptyline is negligible.

It is noted that the aqueous gel A according to the invention has a satisfactory skin penetration profile of amitriptyline and similar to the skin penetration profile of amitriptyline obtained with the comparative cream B.

It is also noted that the bioavailability obtained from composition A and that obtained from composition B are similar.

Example 2

Another pharmaceutical composition in the form of an aqueous gel according to the invention (composition A') was prepared from the ingredients listed in the following table, the quantities being expressed in % by weight.

TABLE 3

| COMPOSITION A' (Invention) | Quantity |
|---|---|
| Amitriptyline hydrochloride | 15 |
| Hydroxyethylcellulose | 1 |
| Propylene glycol | 5 |
| Methylparaben | 0.1 |
| pH agent | Qs pH 5.5 ± 0.5 |
| Water | Qs 100 |

It was observed that the aqueous gel A' according to the invention has a satisfying penetration profile of amitriptyline into the skin and a satisfying bioavailability of amitriptyline.

Example 3

Study of the stability of a formulation C in the form of an aqueous gel (invention) and formulation B in the form of a cream (comparative).

The following aqueous gel (composition C) was prepared from the ingredients listed in the following table, the quantities being expressed in % by weight.

TABLE 4

| COMPOSITION C (Invention) | Quantity |
|---|---|
| Amitriptyline hydrochloride | 10 |
| Hydroxyethylcellulose | 1 |
| Propylene glycol | 5 |
| PEG-7 glyceryl cocoate | 2 |
| pH agent (NaOH, 1N solution) | Qs pH 5.5 ± 0.5 |
| Water | Qs 100 |

The composition B (cream) comprises 10% by weight amitriptyline hydrochloride and 90% by weight Excipial Hydrocrème®, available from the company Galderma, in relation to the total weight of the composition B.

Each of the compositions B and C were placed in an oven at a temperature of 40° C.

The stability of the compositions was then visually assessed over time (at $T_0$, at the time of entry into the oven; at $T_{24h}$, 24 hours after entry into the oven; and at $T_{3\ months}$, 3 months after entry into the oven).

The results are summarised in the table below.

TABLE 5

| | Aspect | | |
|---|---|---|---|
| Compositions | at $T_0$ | at $T_{24\ h}$ | at $T_{3\ months}$ |
| Composition B (Comparative) | White, opaque oil-in-water emulsion | Phase shift observed. The upper oily phase is white and opaque. The lower aqueous phase is transparent | NA |
| Composition C (Invention) | Colourless translucent gel | Translucent gel | Translucent gel |

No syneresis was observed for composition C as an aqueous gel according to the invention after 3 months at 40° C.

A phase shift of the comparative composition B as an oil-in-water emulsion was also observed after only 24 hours at 40° C.

Furthermore, a full stability study was carried out on composition C according to the invention for 6 months at 40° C.

The results are summarised in tables 6 and 7 below.

TABLE 6

| | | RESULTS | | | |
|---|---|---|---|---|---|
| TESTS | SPECIFICATIONS | T0 | T1 month | T3 months | T6 months |
| Visual appearance | Colourless translucent gel | Colourless translucent gel | Colourless translucent gel | Colourless translucent gel | Colourless translucent gel |
| pH | 4.5 to 6.0 | 5.5 | 5.6 | 5.5 | 5.3 |
| Viscosity | 450 to 1500 mPa · s | 1039 mPa · s | 883 mPa · s | 765 mPa · s | 756 mPa · s |
| Dose of amitriptyline HCl | 95.0 mg/g to 105.0 mg/g | 102.7 mg/g | 99.9 mg/g | 99.6 mg/g | 100.6 mg/g |

TABLE 7

| Degradation products of amitriptyline HCl | | RESULTS | | | |
|---|---|---|---|---|---|
| | SPECIFICATIONS | T0 | T1 month | T3 months | T6 months |
| Cyclobenzaprine | ≤0.1% | <detection limit | <detection limit | <detection limit | <detection limit |
| Dibenzosuberone | ≤0.1% | Not detected | Not detected | Not detected | Not detected |
| Unknown impurities | Deferred if ≤0.1%, None ≤0.2% | Not detected | Not detected | Not detected | Unknown impurity 1 RRT 0.38 min < 0.1%; Unknown impurity 2 |

TABLE 7-continued

| Degradation products of amitriptyline HCl | SPECIFICATIONS | RESULTS | | | |
|---|---|---|---|---|---|
| | | T0 | T1 month | T3 months | T6 months |
| Total Impurities | ≤1% | N/A | N/A | N/A | RRT 0.45 min < 0.1% <0.1% |

No syneresis was observed for composition C in the form of an aqueous gel according to the invention after 6 months at 40° C.

Also no major variation was observed for each of the tests performed.

The good physico-chemical stability of compositions in the form of an aqueous gel according to the invention can thus be noted.

The invention claimed is:

1. A method of treating chemotherapy induced peripheral neuropathy (CIPN) comprising topically administering to a subject in need thereof a pharmaceutical composition comprising:
   a) amitriptyline hydrochloride in an amount of 10 to 15% by weight;
   b) a (poly)hydroxy(C1-C4) alkylcellulose in an amount of 0.5% to 2.5% by weight;
   c) a C2-C8 polyol in an amount of 3 to 6% by weight; and
   d) water;
wherein:
the pH of the composition is between 5 and 6;
the composition is formulated for topical application;
systemic uptake of amitriptyline from the composition is negligible; and
the composition is stable for at least about 6 months.

2. The method of claim 1, wherein the amitriptyline hydrochloride is in an amount of 10% by weight.

3. The method of claim 1, wherein the amitriptyline hydrochloride is in an amount of 15% by weight.

4. The method of claim 1, wherein the (poly)hydroxy($C_1$-$C_4$) alkylcellulose is hydroxyethyl cellulose.

5. The method of claim 4, wherein the hydroxyethyl cellulose is in an amount of 1% by weight.

6. The method of claim 1, wherein the $C_2$-$C_8$ polyol is propylene glycol.

7. The method of claim 6, wherein the propylene glycol is in an amount of 5% by weight.

8. The method of claim 1 further comprising an antibacterial or preservative agent.

9. The method of claim 8, wherein the antibacterial or preservative agent is methylparaben.

10. The method of claim 9, wherein the methylparaben is in an amount of 0.10%.

11. The method of claim 1, wherein the composition is administered to the hands and/or feet of the subject.

* * * * *